United States Patent
Gradl

(10) Patent No.: US 8,454,605 B2
(45) Date of Patent: Jun. 4, 2013

(54) BLOCKING DEVICE FOR A BROKEN OR CRACKED BONE

(75) Inventor: Hans-Georg Gradl, Börgerende (DE)

(73) Assignee: M.O.R.E. Medical Solutions GmbH, Rostock (DE)

( * ) Notice: Subject to any disclaimer, the term of this patent is extended or adjusted under 35 U.S.C. 154(b) by 941 days.

(21) Appl. No.: 11/817,556

(22) PCT Filed: Mar. 1, 2006

(86) PCT No.: PCT/EP2006/001865
§ 371 (c)(1),
(2), (4) Date: Nov. 17, 2008

(87) PCT Pub. No.: WO2006/092287
PCT Pub. Date: Sep. 8, 2006

(65) Prior Publication Data
US 2009/0216283 A1    Aug. 27, 2009

(30) Foreign Application Priority Data

Mar. 1, 2005   (DE) .......................... 10 2005 009 347

(51) Int. Cl.
*A61B 17/86* (2006.01)
(52) U.S. Cl.
USPC ........................................................... 606/62
(58) Field of Classification Search
USPC ................. 606/62–68, 86 R, 87–89, 99, 104, 606/329–220
See application file for complete search history.

(56) References Cited

U.S. PATENT DOCUMENTS

| | | | | |
|---|---|---|---|---|
| 4,016,874 A | * | 4/1977 | Maffei et al. | 606/62 |
| 4,177,524 A | * | 12/1979 | Grell et al. | 606/86 R |
| 4,705,027 A | * | 11/1987 | Klaue | 606/64 |
| 5,053,035 A | * | 10/1991 | McLaren | 606/67 |
| 5,374,235 A | | 12/1994 | Ahrens | |
| 5,562,667 A | * | 10/1996 | Shuler et al. | 606/64 |
| 5,697,930 A | * | 12/1997 | Itoman et al. | 606/62 |
| 6,053,918 A | * | 4/2000 | Spievack | 606/64 |
| 6,322,591 B1 | * | 11/2001 | Ahrens | 623/23.27 |
| 6,793,659 B2 | * | 9/2004 | Putnam | 606/62 |
| 2002/0032445 A1 | * | 3/2002 | Fujiwara | 606/67 |
| 2005/0055024 A1 | * | 3/2005 | James et al. | 606/64 |
| 2005/0107791 A1 | * | 5/2005 | Manderson | 606/62 |
| 2005/0177158 A1 | * | 8/2005 | Doubler et al. | 606/64 |
| 2006/0084999 A1 | * | 4/2006 | Aschmann | 606/64 |

FOREIGN PATENT DOCUMENTS

DE   4205118   7/1993
EP   0118778   9/1984

OTHER PUBLICATIONS

PCT International Search Report dated Jun. 21, 2006.

* cited by examiner

*Primary Examiner* — Thomas C. Barrett
*Assistant Examiner* — Christopher Beccia
(74) *Attorney, Agent, or Firm* — McCarter & English, LLP

(57) ABSTRACT

Locking mechanism for a broken or fractured bone, comprising a medulla nail with a proximal portion which may incorporate perforations and a distal portion, and at least one locking aid, characterized in that the distal portion has a surface structure which is designed so that the bone can be stabilized by means of the medulla nail due to the at least one locking aid acting on the surface structure of the nail through the bone from outside, preferably preventing it from rotating and/or being subjected to axial stress.

40 Claims, 3 Drawing Sheets

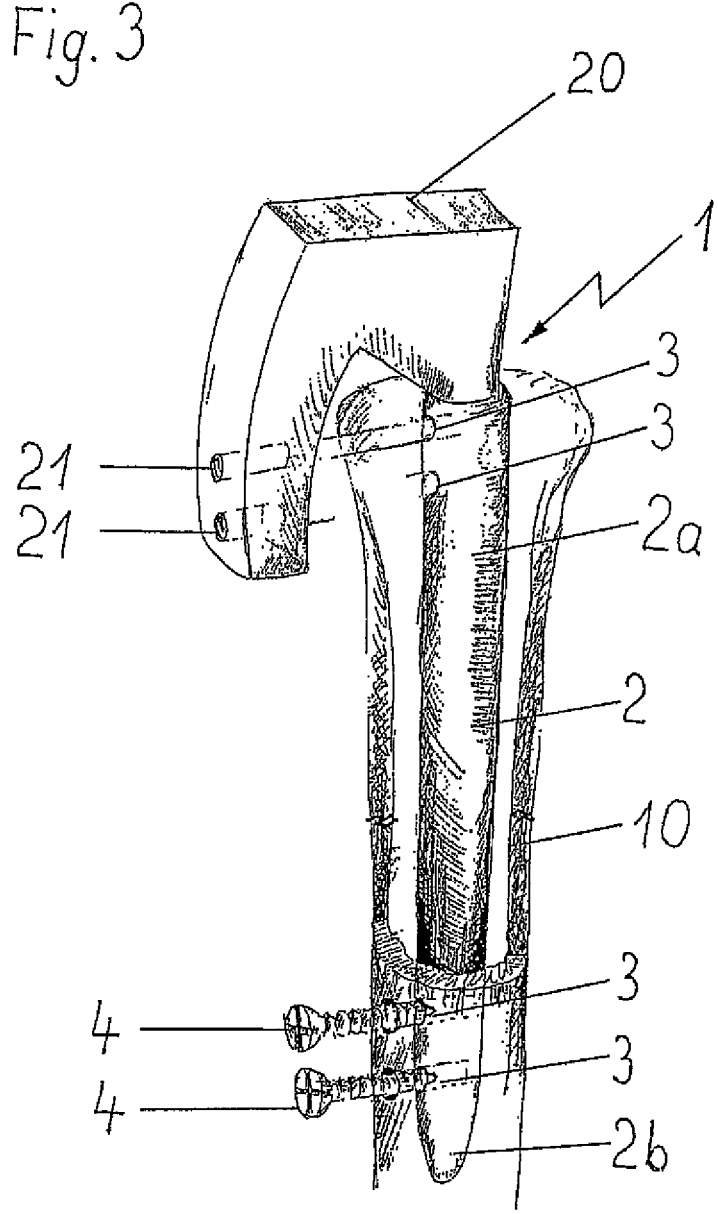

Figure 1A:
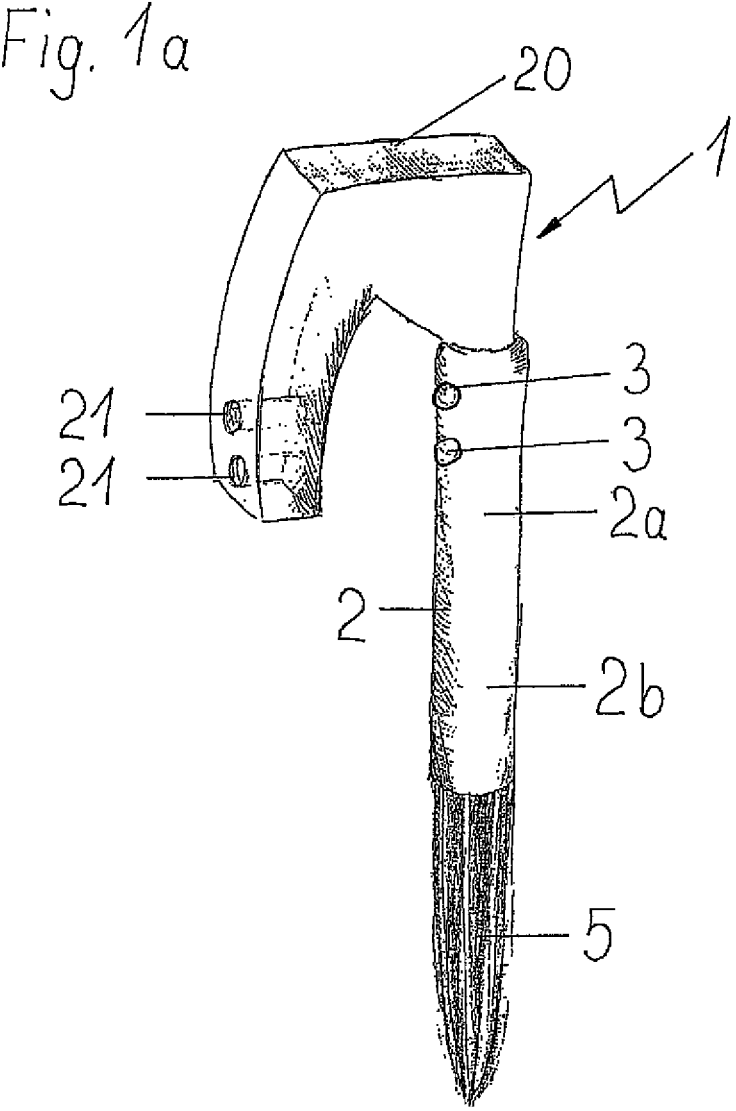

BLOCKING DEVICE FOR A BROKEN OR CRACKED BONE

This invention relates to a locking mechanism for a broken or fractured bone comprising a medulla nail with a proximal portion which may incorporate perforations and a distal portion, and at least one locking aid, of the type outlined in the introductory part of claim 1.

BACKGROUND ART

In principle, other than at infantile age, fractures of long tubular bones are treated by surgery. To this end, a plate of metal or titanium is available on the one hand which, when the plate has been set and adapted to the bone geometry once the fracture has been exposed, can be attached to the bone in order to fix the fracture. On the other hand, intra-medullar stabilisers are being increasingly used, which are also available in different shapes. Medulla nails are also available for treating such fractures.

The fixing principle of such a medulla nail is based on an elastic clamping action between a "rigid" component (bone) and an elastic component (nail), as described in connection with medulla nailing in 1984 by Helms and Naseband in "Ingenieurwissenschaftliche Grundlagen der intramedullaren Osteosynthese" [Engineering principles of intra-medullar osteosynthesis]. The precursor to elastic medulla nailing was G. Küntscher, who tested numerous nail profiles in order to obtain optimum clamping of the nail in the medulla cavity of the bone. Some of these were different from the cylindrical shape of medullar nails used these days. Clover-leaf, triangular or lamellar-type configurations were used. Examples of these nail shapes were illustrated in "Praxis der Marknagelung" [The practice of medulla nailing] by G. Küntscher published in 1962 by Schattauer of Stuttgart. Other examples are illustrated in the journal "Unfallchirurg" [Emergency surgeon] No. 104 on pages 639 to 653 as part of the article published in 2001 entitled "Prinzipien der intramedullaren Knochenbruchstabilisierung" [Principles of intra-medullary bone fracture stabilisation] by C. Krettek. The common purpose of all these profiles is to impart the best possible elastic properties to the medulla nail. In principle, the inserted implant should make the bone fragments as resistant to tilting as possible due to the clamping action in the medulla cavity. This works well with fractures in the middle of the bone. Much more problematic, however, is a break at the bone end because the bone is wider there and less cylindrical in shape than in the middle of the bone. The farther the breaks occur from the bone middle, however, the wider the bone is and also the shorter the distance on which clamping can take place. Another problem is the fact that these implants are not very resistant to torsional forces.

As a result, this shape of elastic medulla nail has been largely abandoned these days, giving way to the use of rigid, less elastic, usually solid nails. The technique currently used as standard for shaft fractures as well as for fractures outside of the middle of the shaft involves inserting a rigid nail from a readily accessible part of the bone which is remote from a fracture. The nail is pushed into the remaining fracture beyond the fracture end and is so as far as the end of the bone. In order to obtain the best possible resistance to axial compression stress and above all stress caused by rotation, the nails are locked on both sides of the fracture, as explained in the above-mentioned article by C. Krettek published in the journal "Unfallchirurg". To achieve this locking effect, the nail has bores extending through the entire diameter and screws serving as locking bolts are introduced firstly into the bone and then inserted in the nail. This is done without the person carrying out the operation having direct sight because the nail is already disposed in the inner region of the bone. In order to find the lock bores, guide fixtures which are calibrated by the manufacturer for the specific nail type, are used as a template, as illustrated in FIG. 3. These guide fixtures are fixedly connected to the beginning of the nail, making it at least possible to find the nail bores at the beginning of the nail. In practical terms, however, this has not been possible using guide fixtures because even a rigid nail bends slightly as it is being introduced into the rigid bony medullary canal.

As a result, these bores in the nail end have been located by viewing them with the aid of intra-operative X-ray imaging in the prior art. This involves a certain amount of X-ray exposure for both the patient and the surgeon and costs valuable time. The prior art described above is explained in the paper published in 2001 in the journal "Radiologe" [Radiologist], No. 411 on pages 91 to 94 entitled "Radiation exposure of the patient by intraoperative imaging of intramedullary osteosyntheses" by N. Suhm, A. L. Jacob, I. Zuna, H. W. Rosner, P. Regazzoni and P. Messmer. If a medulla nail is inserted but not locked, however, it is not possible to obtain sufficient resistance to compression and above all to rotation.

OBJECTIVE OF THE INVENTION

Accordingly, the objective of this invention is to improve the existing nail and nailing technique and in particular to do so without the need for intra-operative X-ray imaging whilst nevertheless enabling reliable locking of the distal end of the nail in the bone.

As proposed by the invention, this objective is achieved on the basis of the features defined in claim 1. Accordingly, a new type of configuration of the nail surface is proposed and it is possible to lock medullary nails of any type; this makes a simple operative method possible.

The advantages which can be achieved by this invention are obtained on the basis of a locking mechanism for a broken or fractured bone comprising a medulla nail with a proximal portion which may be provided with perforations and a distal portion, and at least one locking aid. The distal portion of the medulla nail of the locking mechanism also has a surface structure which is designed so that the bone can be stabilised by means of the medulla nail due to the at least one locking aid acting through the bone on the surface structure of the nail from outside, preferably preventing rotation and/or axial stress. The surface structure makes it possible to make accurate contact with the surface structure of the medulla nail by means of the locking mechanism without having to resort to conventional X-ray imaging and, as a result, proceed with a defined and reliable locking of the medulla nail to the bone. This being the case, the locking mechanism no longer has to make exact contact with the bores conventionally disposed on the proximal portion and located by X-ray imaging and instead, the surface structure of the medulla nail affords the locking mechanism a sufficient surface on which to act so as to obtain a reliable and stable fixed positioning of the medulla nail inside the bone. The locking mechanism proposed by the invention thus requires significantly less apparatus than is required for conventional medullary nailing. Consequently, costs are lower and time is also saved. A major advantage is the fact that additional radiation exposure is also avoided because there is no need for X-ray imaging.

As proposed by the invention, the medulla nail is of a longitudinally extending pin-shaped design and the cross-section of the medulla nail is essentially cylindrical. The cross-section of the medulla nail may also be such that it is longer in one direction of its longitudinal extension than in the other direction of longitudinal extension. Not only does this design of cross-section enable easy insertion of the medulla nail in the bone, it also contributes to producing a high stability of the medulla nail itself. As a result of this design, the quantity of bone marrow displaced is reduced to a minimum.

The cross-section of the medulla nail may be essentially oval but an essentially elliptical cross-section of the medulla nail is also possible. Due to these different design options, the medulla nail can be readily adapted to the respective shape of the bone. For the purpose of the invention, the cross-section of the medulla nail is that of a hollow profile. Not only does the hollow profile lead to higher stability of the medulla nail, it also saves on weight.

The cross-section of the medulla nail may also be essentially V-shaped. The V-shaped design of the cross-section of the medulla nail makes for easy introduction into the bone, as a result of which the medulla nail causes only a slight displacement of the bone marrow. The locking aid may act both in the direction of the side faces or flanks and in the direction of the indentations formed in the side faces or flanks. In this respect, the locking aids preferably subtend an angle of 90° respectively with the respective side face or flank. The locking aid acting in the direction towards the indentation is symmetrically oriented so that the mid-line of the locking aid acting on the indentation bisects the imaginary surface extending between the side faces or flanks into two identical triangles, if the V-shaped nail profile is viewed in the direction towards the bisection surface. The indentation fulfils a guiding function for the locking aid and the legs of the V-shaped nail profile afford the locking aids a large and easy-to-locate attacking surface. Using three locking aids results in a particularly preferred three-point anchoring. Depending on the application (type of fracture, bone size) however, it would also be possible to use one, two or more than three locking aids.

As proposed by the invention, the external circumference of the medulla nail is coated with a material which the at least one locking aid is able to penetrate to establish a positive connection, and the coating material may be a softer material than the material of the medulla nail, preferably a metal or a plastic material. The softer material constitutes a material bed for the locking aid, into which the locking aid can work itself depending on its shape. This additional tolerance when securing the locking aid makes it easier to secure and set the position of the medulla nail, thereby guaranteeing the reliability of the connection.

The surface structure of the distal portion preferably occupies one third or one quarter or one fifth of the nail length. However, the surface structure of the distal portion may also comprise a region which extends as far as the perforations of the proximal portion. The fact that the surface structure is disposed in a specific region means that there are sufficient possibilities for the locking aid to make contact with the medulla nail and then establish a reliable connection to the medulla nail.

For the purpose of the invention, the surface structure has grooves extending parallel with the longitudinal extension of the medulla nail. The grooves are preferably uniformly distributed around the circumference of the medulla nail. The purpose of the grooves is to prevent the medulla nail from turning and protect it from torsional stress by affording a positive connection when the at least one locking aid locates in one of the grooves and acts as an axial lock due to a force fit.

As proposed by the invention, the surface structure has transversely extending grooves around the circumference, preferably at approximately 90° with respect to the axial direction of the nail length. These grooves prevent the position of the medulla nail from shifting in the direction of its longitudinal axis, primarily due to a positive connection, and from rotating due to a force fit. In particular, it is necessary to prevent any longitudinal shifting of the medulla nail. The grooves preferably have a V-shaped cross-section. These grooves are preferably used to accommodate locking aids with a conical tip, thereby establishing a positive connection. It is also preferable if the grooves have a U-shaped cross-section. These grooves are preferably used to accommodate locking aids with a spherical tip, thereby establishing a positive connection.

The contour of the groove preferably varies in an alternating manner in its longitudinal direction in terms of width and depth. Depending on the direction in which it is disposed, the groove prevents the medulla nail from turning and/or shifting longitudinally. It is also preferable if the grooves have a periodically varying contour in terms of their cross-section and their depth.

For the purpose of the invention, the grooves have a constant contour. This produces a strong clamping action between the locking aid and groove. In their longitudinal direction, the grooves preferably have alternating portions of differing width with a long groove depth and narrow portions with a short groove depth. This produces a positive connection between the locking aid and medulla nail, preventing both axial shifting and turning.

The surface structure is preferably of a shape incorporating indentations. It is also preferable if the surface structure has semispherical indentations. The surface structure may preferably have spherical indentations. The surface structure may also have pyramid-shaped indentations. Furthermore, the surface structure may have tetrahedral indentations. This shape of the surface structure akin to a golf ball structure complements a co-operating shape of the tip of the locking aid, producing not only a non-positive but additionally also a positive connection between the locking aid und medulla nail.

It is naturally also possible for the medulla nail with the surface structure proposed by the invention also to be provided with the conventional perforations at its distal portion. This gives the surgeon the option of introducing the medulla nail using either the new method or alternatively the method used to date.

As proposed by the invention, the at least one locking aid actively connected to the medulla nail can preferably be oriented at approximately 90° with respect to the nail axis and in the direction towards the mid-line of the medulla nail. Slight variations in the inclination of the locking aid are permissible. Furthermore, as a result of the invention, the at least one locking aid which can be actively connected to the medulla nail can be located by means of the surface structure of the distal portion, preferably under pressure and/or preferably without any clearance.

For the purpose of the invention, the at least one locking aid actively connected to the medulla nail has a tip. The tip of the locking aid is preferably designed so that it is able to establish a positive connection with the medulla nail by means of the surface structure of the distal portion. In order to establish the positive connection, appropriate designs of the shape of the golf-ball-type surface structure are used in conjunction with the tip of the locking aid. For example, a spherical tip of the locking aid will require a surface structure with approximately semispherical indentations. Furthermore, the tip of the locking aid is preferably designed so that it is able to establish a non-positive connection with the medulla nail by means of the surface structure of the distal portion. This results in a particularly reliable connection in addition to the positive connection.

As proposed by the invention, the at least one locking aid which can be actively connected to the medulla nail is preferably designed so that it is able to penetrate the bone wall. Preferably, the at least one locking aid which can be actively connected to the medulla nail is designed so it can be anchored in the bone wall.

As proposed by the invention, the at least one locking aid which can be actively connected to the medulla nail is designed so that in its position securing the medulla nail, it does not project out beyond the outer bone wall or does so only slightly. This is very important because the point of fracture must be covered again and rendered sterile and parts of the medulla nail extending through the skin could lead to infections.

The at least one locking aid is preferably a screw, designed so that it can be located with the surface structure of the distal portion. It is also preferable if the screw has a spherical, preferably rounded tip. Furthermore, the screw may have a conical or a frustoconical tip. In order to establish the positive connection, appropriate designs of the shape of the golf-ball-type surface structure co-operate with the tip of the screw. For example, a spherical tip of the screw will require a surface structure with semispherical indentations. The tip of the screw is preferably also designed so that it is able to establish a non-positive connection with the medulla nail by means of the surface structure of the distal portion. This results in a particularly reliable connection in addition to the positive connection. It is preferable to use three screws because this results in a particularly preferred three-point anchoring. Depending on the application (type of fracture, bone size) however, it is also possible to use one, two or more than three screws.

For the purpose of the invention, the screw is a threaded screw with a self-tapping thread which can be positively and/or non-positively connected to the bone wall.

The thread is preferably on only a region of the screw bolt which can be connected to the bone wall, and the diameter of the region of the screw bolt which does not have a thread is smaller than the external diameter of the thread. The region of the screw bolt which can be connected to the bone wall should have a thread length which is preferably slightly longer than the diameter of the bone wall. The ratio of the thread length to the bone wall is high so that the screw bolt locates effectively and reliably with the bone wall. The thread may be a metric thread. However, other expedient thread types are also possible.

The screw preferably has a hardened tip. It is also preferable if the hardened tip or front end of the screw is provided with a circumferentially extending, self-tapping cutting edge. The tip of the screw is therefore able to work itself into the material of the medulla nail, which increases the strength of the connection.

DESCRIPTION OF PREFERRED EMBODIMENTS

Figure 1B:
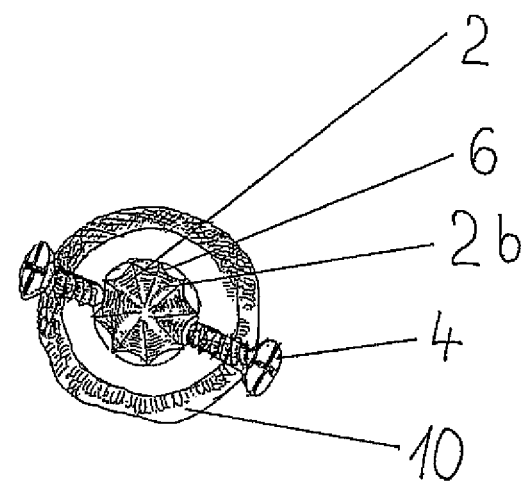
Figure 2A:
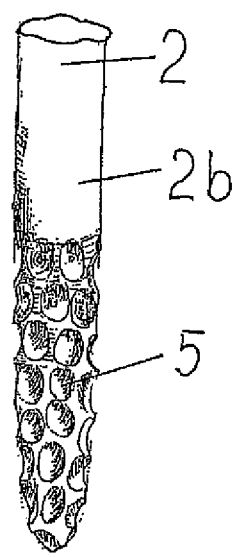
Figure 2B:
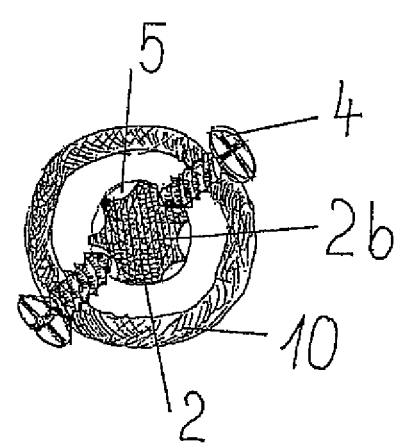

The invention will be described in more detail below on the basis of preferred embodiments with reference to the appended drawings. The features, objectives and advantages of the invention will be explained. Of the drawings:

FIG. 1a is a perspective view from the side showing a first embodiment of the locking mechanism proposed by the invention FIG. 1b is a view of the first embodiment of the locking mechanism seen from underneath with the locking aid proposed by the invention fitted and the bone illustrated in section FIG. 2a shows an exploded side view of a second embodiment of the locking mechanism proposed by the invention FIG. 2b is a view of the second embodiment of the locking mechanism seen from underneath with the locking aid proposed by the invention fitted and the bone illustrated in section FIG. 3 is a perspective side view of a conventional locking mechanism with the bone shown in partial section.

In the description below, the same reference numbers are used in the individual drawings to refer to what are essentially the same parts.

FIG. 3 is a diagram illustrating a perspective side view of a conventional locking mechanism 1 with a diagram of the bone seen in partial section representing a broken or fractured bone 10. The conventional locking mechanism 1 comprises a medulla nail 2 with a proximal portion 2a which may incorporate perforations 3 and a distal portion 2b, and at least one locking aid 4. The medulla nail 2 is introduced into the bone 10 and thus finally reaches an end position, as illustrated in FIG. 3. Having reached the end position inside the bone, a guide fixture 20 serving as an aid to obtaining the correct aim is placed on the medulla nail 2. The guide fixture 20 is thus accommodated in the medulla nail 2 in an exact fit and mounted so that it can not turn in the medulla nail 2.

In order to fit the guide fixture 20 on the medulla nail 2 so that it can not turn, the medulla nail 2 may have co-operating grooves (not illustrated), in which projections (not illustrated) provided on the guide fixture 20 can locate. Conversely, the medulla nail 2 could have projections (not illustrated) which locate in grooves (not illustrated) provided on the guide fixture 20. In the case of conventional locking mechanisms 1, both the distal portion 2a and the proximal portion 2b of the medulla nail 2 have perforations 3. Once the defined position of the medulla nail 2 has been determined and the guide fixture 20 fitted as described above, the bone 10 can be bored in order to stabilise the medulla nail by means of at least one locking aid, such as locking aids in the form of screws 4 described below. To this end, a drill is fed respectively through the bores 21 incorporated in the guide fixture 20. Having penetrated the bone wall, the bores 21 allow the drill to make contact exactly with the perforations 3 which already exist on the proximal portion 2a of the medulla nail 2.

The perforations 3 on the distal portion 2b of the conventional medulla nail 2 can only be rendered visible by means of X-rays, which involves additional exposure of the broken or fractured bone 10 and the area around it to radiation. Once the perforations 3 on the distal portion 2b of the medulla nail 2 have been located by X-ray imaging in the conventional manner, these positions of the perforations can be marked in order to bore through the bone wall with the correct aim. Once the bone wall has been bored, the at least one locking aid in the form of a screw 4 can be fixed in the bone wall to enable the bone 10 to be finally stabilised by means of the medulla nail 2.

FIG. 1a shows a perspective view from the side of a first embodiment of the locking mechanism 1 proposed by this invention. The locking mechanism 1 illustrated in FIG. 1a for a broken or fractured bone, such as the bone 10 illustrated in FIG. 3, comprises a medulla nail 2 with a proximal portion 2a which may incorporate perforations 3 and a distal portion 2b, with which at least one locking aid in the form of a screw 4 (FIG. 1b) can cooperate. The medulla nail 2 is introduced into the bone 10 (FIG. 3) and thus finally reaches an end position, as illustrated in FIG. 3. Once the end position inside the bone is reached, a guide fixture 20 serving as a guiding tool is placed on the medulla nail 2. The guide fixture 20 is accommodated in the medulla nail 2 in an exact fit and mounted in the medulla nail 2 so that it is not able to turn.

In order to fit the guide fixture 20 on the medulla nail 2 so that it is not able to turn, the medulla nail 2 may have appropriate grooves (not illustrated) in which projections (not illustrated) provided on the guide fixture 20 can locate. Conversely, the medulla nail 2 could naturally have projections (not illustrated) which can locate in grooves (not illustrated) provided in the guide fixture 20. As proposed by the invention, only the proximal portion 2a of the medulla nails 2 has perforations, as illustrated in FIG. 1a. Once the defined position of the medulla nail 2 has been determined and the guide fixture 20 has been fitted as described above, the bone 10 can be bored in order to stabilise the medulla nail by means of the at least one locking aid in the form of a screw. To this end, a drill is fed respectively through bores 21 incorporated in the guide fixture 20. Having penetrated the bone wall, the bores 21 allow the drill to make contact exactly with the perforations 3 which already exist on the proximal portion 2a of the medulla nail 2, as illustrated in FIG. 3.

The distal portion 2b of the medulla nail 2 has a surface structure 5 with longitudinal grooves 6 (FIG. 1b), which are designed so that the bone 10 (FIG. 1b) can be stabilised, preferably to prevent it from being rotated and/or subjected to axial stress, by means of the medulla nail 2 via the at least one locking aid in the form of a screw 4 (FIG. 1b) acting through the bone 10 (FIG. 11b) on the surface structure 5 of the medulla nail 2 from outside. Since the surface structure 5 has longitudinal grooves across a defined region of the longitudinal extension of the medulla nail 2, the bone 10 can be bored at a co-operating region, thereby ensuring that the at least one locking aid in the form of a screw 4 (FIG. 1b) makes contact with the surface structure 5 of the medulla nail 2 incorporating the longitudinal grooves 6 with a correct aim. As a result, the medulla nail 2 can be readily stabilised. The screw is anchored in the bone wall due to the self-tapping thread provided on it.

The medulla nail 2 is of a longitudinally extending pin-type shape. The cross-section of the medulla nail 2 is essentially cylindrical, as illustrated in FIG. 1b.

Instead of the longitudinal grooves, the external circumference of the medulla nail 2 may be provided with a region having a surface structure 5 illustrated in FIG. 1a, coated with a material (not illustrated), which the at least one locking aid 4 is able to penetrate and establish a positive connection, in which case the coating material is a softer material than the material of the medulla nail 2, preferably a metal or a plastic material.

The surface structure 5 of the distal portion 2b of the medulla nail 2 illustrated in FIG. 1a occupies one third or one quarter or one fifth of the nail length. However, the surface structure 5 of the distal portion 2b may also occupy a region extending as far as the perforations 3 of the proximal portion 2a of the medulla nail 2.

FIG. 1b illustrates a view of the first embodiment of the locking mechanism 1 proposed by the invention from underneath with a diagram of the bone in section. In the case of the medulla nail 2 illustrated in FIG. 1b, the surface structure 5 has grooves 6 extending parallel with the longitudinal extension of the medulla nail 2. The grooves 6 are preferably distributed uniformly around the circumference of the medulla nail 2. Two screws 4 offset from one another by 180° serving as a locking aid locate in the grooves 6. This number of locking aids is merely given by way of example. It would naturally be possible to use one, three or more than three locking aids, irrespective of the respective application. As illustrated in FIG. 1b, the locking aids 4 each have a thread, which is anchored in the wall of the bone 10.

Another embodiment differs from the embodiment illustrated in FIG. 1b due to the fact that the surface structure 5 has grooves (not illustrated) extending transversely, preferably circumferentially, at approximately 90° with respect to the axial direction of the nail length.

The grooves 6 preferably have a V-shaped cross-section. However, the grooves 6 may also have a U-shaped cross-section, as illustrated in FIG. 1b.

The contour of the groove may be variable in an alternating manner in its longitudinal extension in terms of the width and depth. The grooves may also have a contour which varies periodically in terms of its cross-section and its depth.

In the case of another embodiment, the grooves have a constant contour, as may be seen from FIG. 1a.

FIG. 2a illustrates a side view of a second embodiment of the locking mechanism 1 based on the invention. To avoid redundancy, reference may be made to the description given in connection with FIG. 1a. In the case of the locking mechanism 1 illustrated in FIG. 2a, the surface structure 5 is provided in the form of a plurality of indentations distributed both around the circumference of the medulla nail and in its longitudinal extension. The indentations may be of a semi-spherical shape or spherical shape.

The surface structure 5 may naturally also have pyramid-shaped or tetrahedral indentations.

FIG. 2b shows a view of the second embodiment of the locking mechanism 1 proposed by the invention from underneath with a diagram of the bone shown in section. Two locking aids in the form of screws 4 disposed offset from one another by 180° locate in the indentations of the surface structure 5. This number of locking aids is merely given by way of example. Naturally, it would also be possible to use one, two or more than three locking aids, depending on the respective application. As illustrated in FIG. 1b, each of the locking aids 4 has a thread, which can be anchored in the wall of the bone 10.

The at least one locking aid in the form of a screw 4 which can be actively connected to the medulla nail can preferably be oriented at approximately 90° with respect to the nail axis and in the direction towards the mid-line of the medulla nail 2. The at least one locking aid in the form of a screw 4 which can be actively connected to the medulla nail 2 can be located by means of the surface structure 5 of the distal portion 2b, preferably under pressure and/or without any clearance.

The at least one locking aid 4 which can be actively connected to the medulla nail 2 has a tip. The tip of the locking aid 4 is designed so that it is able to establish a positive connection with the surface structure 5 of the distal portion 2b. The tip of the locking aid 4 is designed so that it is also able to establish a non-positive connection with the medulla nail 2 by means of the surface structure 5 of the distal portion 2b.

The at least one locking aid 4 which can be actively connected to the medulla nail 2 is designed so that it is able to penetrate the bone wall. The at least one locking aid in the form of a screw 4 which can be actively connected to the medulla nail 2 is designed so that it can be anchored in the bone wall.

The at least one locking aid 4 which can be actively connected to the medulla nail is designed so that in its position securing the medulla nail 2, it preferably does not project beyond the outer bone wall or does so only slightly, as may be seen from FIG. 2b.

The screw 4 may be a hollow set screw, for example.

The screw has a spherical, preferably rounded tip. The screw may also have a conical or a frustoconical tip. The screw is a threaded screw with a self-tapping thread which can be positively and/or non-positively connected to the bone wall. The screw may also have a hardened tip. This being the case, the hardened tip is provided with a circumferentially extending, self-tapping cutting edge.

What is claimed is:

1. Locking mechanism for a broken or fractured bone, comprising:
   a medulla nail with a proximal portion and a distal portion, and
   at least one locking aid,
   wherein the distal portion has an outer surface structure which is designed so that the bone can be stabilised by means of the medulla nail due to the at least one locking aid configured to extend through the bone to be in contact with at least a portion of the outer surface structure of the medulla nail, thereby preventing the medulla nail from being rotated or subjected to axial stress;
   wherein the medulla nail has a longitudinally extending shape;
   wherein the outer surface structure has grooves distributed around the external circumference of the outer surface structure, the grooves extending parallel with the longitudinal extension of the medulla nail; and
   wherein the at least one locking aid contacts at least one groove of the outer surface structure of the distal portion, without extending through the medulla nail, to thereby prevent the medulla nail from being rotated or subjected to axial stress.

2. Locking mechanism as claimed in claim 1, characterised in that the cross-section of the medulla nail is essentially cylindrical.

3. Locking mechanism as claimed in claim 1, characterised in that the medulla nail has a cross-section such that one direction of extension is longer than the other direction of extension.

4. Locking mechanism as claimed in claim 3, characterised in that the cross-section of the medulla nail is essentially oval.

5. Locking mechanism as claimed in claim 3, characterised in that the cross-section of the medulla nail is of an essentially elliptical shape.

6. Locking mechanism as claimed in claim 1, characterised in that the cross-section of the medulla nail has a hollow profile.

7. Locking mechanism as claimed in claim 1, characterised in that the cross-section of the medulla nail is approximately V-shaped.

8. Locking mechanism for a broken or fractured bone, comprising:
   a medulla nail with a proximal portion and a distal portion; and
   at least one locking aid;
   wherein the distal portion has an outer surface structure which is designed so that the bone can be stabilised by means of the medulla nail due to the at least one locking aid configured to extend through the bone to be in contact with at least a portion of the outer surface structure of the medulla nail without extending through the medulla nail, thereby preventing the medulla nail from being rotated or subjected to axial stress;
   wherein the external circumference of the outer surface structure is coated with a material which the at least one locking aid is able to penetrate without extending through the medulla nail in order to establish a positive connection, and the coating material is a softer material than the material of the medulla nail.

9. Locking mechanism as claimed in claim 8, characterised in that the medulla nail has a longitudinally extending shape.

10. Locking mechanism as claimed in claim 1, characterised in that the outer surface structure of the distal portion occupies one third or one quarter or one fifth of the nail length.

11. Locking mechanism as claimed in claim 8, wherein the coating material is a metal or a plastic material.

12. Locking mechanism as claimed in claim 1, characterised in that the grooves are distributed uniformly around the external circumference of the outer surface structure.

13. Locking mechanism for a broken or fractured bone, comprising:
   a medulla nail with a proximal portion and a distal portion; and
   at least one locking aid;
   wherein the distal portion has an outer surface structure which is designed so that the bone can be stabilised by means of the medulla nail due to the at least one locking aid configured to extend through the bone to be in contact with at least a portion of the outer surface structure of the medulla nail, thereby preventing the medulla nail from being rotated or subjected to axial stress;
   wherein the outer surface structure has grooves distributed around the external circumference of the outer surface structure, the grooves extending transversely relative to the axial direction of the medulla nail length; and
   wherein the at least one locking aid contacts at least one groove of the outer surface structure of the distal portion, without extending through the medulla nail, to thereby prevent the medulla nail from being rotated or subjected to axial stress.

14. Locking mechanism as claimed in claim 12, characterised in that the grooves have a V-shaped or U-shaped cross-section.

15. Locking mechanism as claimed in claim 13, characterised in that the grooves have a V-shaped or U-shaped cross-section.

16. Locking mechanism as claimed in claim 1, characterised in that the contour of the groove is variable in an alternating manner in its longitudinal direction in terms of width and depth.

17. Locking mechanism as claimed in claim 16, characterised in that the grooves have a periodically varying contour in terms of their cross-section and their depth.

18. Locking mechanism as claimed in claim 1, characterised in that the grooves have a constant contour.

19. Locking mechanism as claimed in claim 16, characterised in that the grooves have alternating wide portions with a big groove depth and narrow portions with a short groove depth.

20. Locking mechanism for a broken or fractured bone, comprising:
   a medulla nail with a proximal portion and a distal portion; and
   at least one locking aid;
   wherein the distal portion has an outer surface structure which is designed so that the bone can be stabilised by means of the medulla nail due to the at least one locking aid configured to extend through the bone to be in contact with at least a portion of the outer surface structure of the medulla nail, thereby preventing the medulla nail from being rotated or subjected to axial stress;

wherein the outer surface structure is of a shape incorporating indentations, the indentations distributed around the external circumference of the outer surface structure; and wherein the at least one locking aid contacts at least one indentation of the outer surface structure of the distal portion, without extending through the medulla nail, to thereby prevent the medulla nail from being rotated or subjected to axial stress.

21. Locking mechanism as claimed in claim 20, characterised in that the outer surface structure has semispherical indentations.

22. Locking mechanism as claimed in claim 20, characterised in that the outer surface structure has spherical indentations.

23. Locking mechanism as claimed in claim 20, characterised in that the outer surface structure has pyramid-shaped indentations.

24. Locking mechanism as claimed in claim 20, characterised in that the outer surface structure has tetrahedral indentations.

25. Locking mechanism as claimed in claim 1, characterised in that the at least one locking aid which is in contact with the medulla nail is oriented at approximately 90° with respect to the medulla nail axis and in the direction towards the mid-line of the medulla nail.

26. Locking mechanism as claimed in claim 1, characterised in that the at least one locking aid which is configured to be in contact with the medulla nail can be located with the outer surface structure of the distal portion, under pressure or without any clearance.

27. Locking mechanism as claimed in claim 1, characterised in that the at least one locking aid has a tip.

28. Locking mechanism as claimed in claim 27, characterised in that the tip of the locking aid is designed so that it is able to establish a positive or non-positive connection with the medulla nail by means of the outer surface structure of the distal portion.

29. Locking mechanism as claimed in claim 13, wherein the at least one locking aid has a tip; and wherein the tip of the locking aid is designed so that it is able form a positive or non-positive connection with the medulla nail by means of the outer surface structure of the distal portion.

30. Locking mechanism as claimed in claim 13, wherein the grooves extend transversely around the external circumference of the outer surface structure at about an angle of 90° relative to the axial direction of the medulla nail length.

31. Locking mechanism as claimed in claim 1, characterised in that the at least one locking aid is designed so that it can be anchored in the bone wall.

32. Locking mechanism as claimed in claim 13, wherein the grooves have alternating wide portions with a big groove depth and narrow portions with a short groove depth.

33. Locking mechanism as claimed in claim 1, characterised in that the at least one locking aid is a screw which is designed so that it can be in contact with at least one groove of the outer surface structure of the distal portion.

34. Locking mechanism as claimed in claim 33, characterised in that the screw has a spherical, rounded tip;

wherein the tip is configured and dimensioned to be in contact with the outer surface structure of the distal portion.

35. Locking mechanism as claimed in claim 33, characterised in that the screw has a conical or frustoconical tip;

wherein the tip is configured and dimensioned to be in contact with the outer surface structure of the distal portion.

36. Locking mechanism as claimed in claim 13, wherein the at least one locking aid is a screw which is designed so that it can be in contact with at least one groove of the outer surface structure of the distal portion.

37. Locking mechanism as claimed in claim 33, characterised in that the screw is a threaded screw with a self-tapping thread, which can be positively or non-positively connected to the bone wall.

38. Locking mechanism as claimed in claim 37, characterised in that the thread is disposed on only a region of the screw bolt which can be connected to the bone wall, and the diameter of the region of the screw bolt which does not have a thread is shorter than the external diameter of the thread.

39. Locking mechanism as claimed in claim 38, characterised in that the screw has a hardened tip; and wherein the hardened tip is provided with a circumferentially extending self-tapping cutting edge.

40. Locking mechanism as claimed in claim 13, wherein the at least one locking aid is a screw which is designed so that it can be in contact with at least one groove of the outer surface structure of the distal portion;

wherein the screw is a threaded screw with a self-tapping thread, which can be positively or non-positively connected to the bone wall; and wherein the thread is disposed on only a region of the screw bolt which can be connected to the bone wall, and the diameter of the region of the screw bolt which does not have a thread is shorter than the external diameter of the thread.

* * * * *